Nov. 11, 1958 R. E. SHEPHERD Plant Pat. 1,770
ROSE PLANTS
Filed Sept. 5, 1957
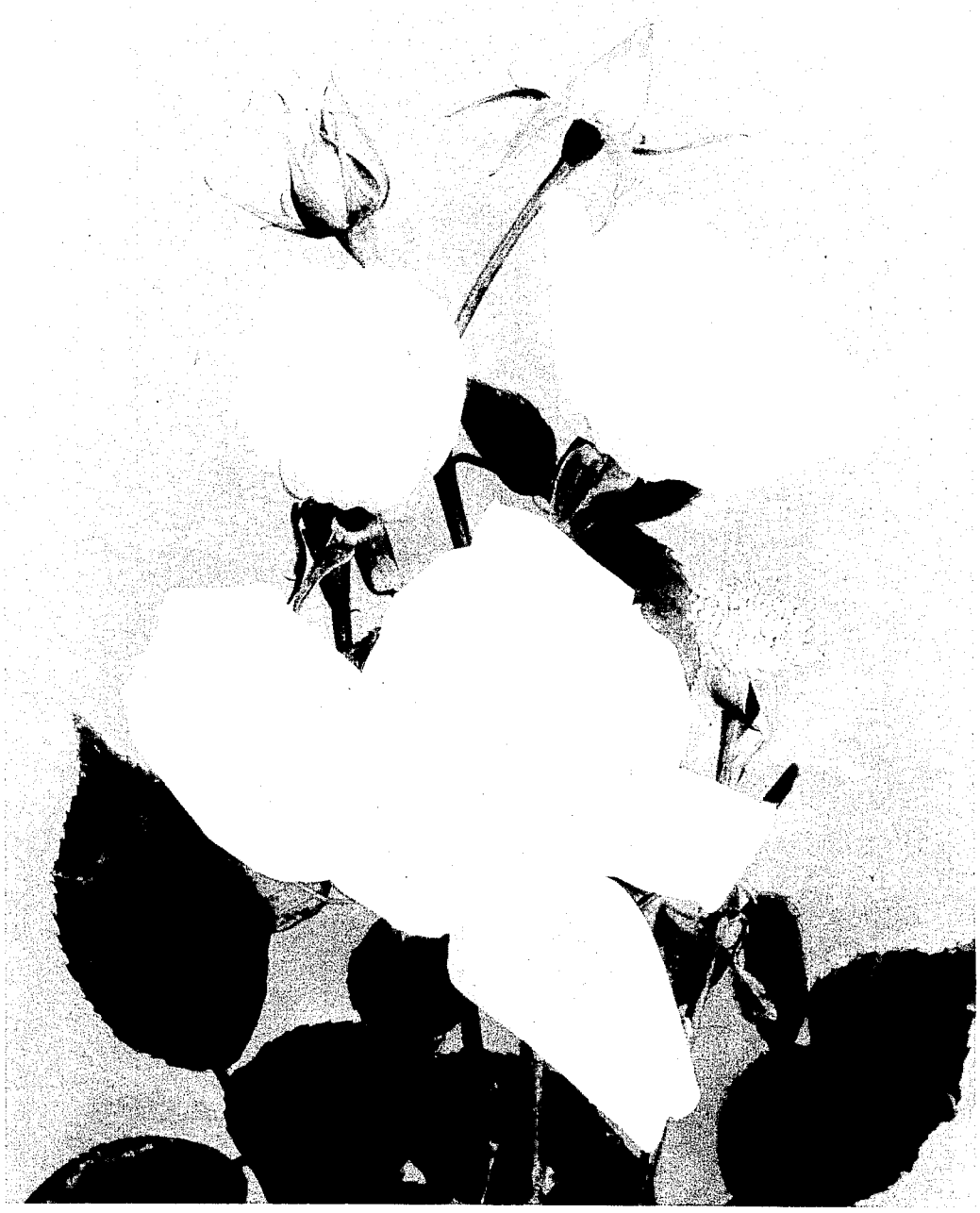
INVENTOR
Roy E. Shepherd
By Orville M. Kile
Plant Patent Agent United States Patent Office Plant Pat. 1,770
Patented Nov. 11, 1958

1,770

ROSE PLANTS

Roy E. Shepherd, Medina, Ohio, assignor to Edith C. Bosley, Mentor, Ohio

Application September 5, 1957, Serial No. 682,266

1 Claim. (Cl. 47—61)

My present invention relates to a new type of rose plant known as Grandiflora. This new variety is the first white rose of the Grandiflora class, so far as I know, and is an exceedingly prolific producer of large, fragrant, semi-double, hybrid-tea type white blooms which grow in clusters or candelabra. It is more productive of bloom than any other Grandiflora in my garden.

This new variety is the result of direct breeding effects made by me at my gardens and greenhouses near Medina, and its parentage is Madam Butterfly (unpatented) × New Dawn (Plant Patent No. 1) × Crimson Glory (Plant Patent No. 105). The bush is extremely vigorous and averages 3 to 4 feet in height in my nursery. If left unpruned, it would probably grow taller and in mild climates, where the canes are not injured in winter, sometimes grows to a height of 6 to 7 feet. This leads us to believe that it can be grown as a climber in the warmer climates.

This variety has been asexually reproduced by me by the budding method, in my Medina nurseries, and its distingishing characteristics appear to be permanent.

The accompanying illustration shows in approximately true colors, buds and blossoms of my new variety in various stages of opening, with portions of the stems and foliage. Also shown are the stamens and pistils of a flower from which the petals have been stripped.

In the following detailed description, color plate references indicate Ridgway's Color Standards and Nomenclature. Other use of color names indicates the usual directionary means of the term.

*The plant*

Growth habits: Very vigorous and strong, in this climate producing a bush twice the size of an ordinary hybrid tea, and it has attained a height of seven feet where canes are not injured by winter cold.

Blooming habit: Very prolific, in a single season bearing hundreds of large, fragrant, white blooms in clusters of 3 to 7.

Disease resistance: My new variety has proven more resistant to all forms of blackspot than most varieties. Grown under the same conditions in my gardens, the resistance of my new variety to blackspot is much greater than that of the variety Queen Elizabeth (Plant Patent No. 1,259), which is known as a disease-resistant variety. Among the white rose varieties, two of the well-known ones found much less resistant to blackspot than my new variety are Kaiserin Auguste Viktoria (unpatented) and Rex Anderson (Plant Patent No. 335). Since mildew and other rose diseases are no problem in my garden, I do not know how my new variety compares with others in respect to them, but its leaf texture suggests that it would be quite resistant to diseases of all kinds.

Form: Tall, vigorous, upright bush, with a possibility of being grown as a climbing rose in milder climates.

Foliage:

*Quantity.*—Abundant.

*Type.*—Odd-pinnately compound, with 3 to 7 leaflets, usually 5.

*Size.*—Largest terminal leaflets approximately 3 inches by 1⅞ inches. Lateral leaflets much smaller.

*Texture.*—Leathery.

*Edge.*—Undulate, with very sharp serrations which sometimes are almost like prickles.

*Color.*—Deep Dull Yellow Green to Dark Dull Yellow Green (both Plate XXII), on upper surface, with under surface Hellebore Green (Plate XXVI) to Cerro Green (Plate V), and edge usually tinged with red.

*Stipules.*—Narrow; long; clinging, except for small, sharp points.

*Leaf stem.*—Very short from last leaflet to stem; stipule often occupies entire length.

Stems:

*Strength.*—Main stems are very strong and heavy; branches progressively smaller as flowers are approached. Stems or canes grow long where winter weather does not kill them back.

*Color.*—Young stem is Chromium Green (Plate XXXII); old stem Cerro Green (Plate V) partly overlaid with Violet Carmine (Plate XII).

*Thorns.*—Huge sharp thorns are closely and irregularly spaced. They point slightly downward and are tinged with shades of red ranging from Rose Red to Pomegranate Purple (both Plate XII).

*The flower*

Bud:

*Size.*—Small, approximately ¾ inch as calyx breaks.

*Opening.*—Slow and even.

*Color.*—Greenish-white (approximately Light Turtle Green—Plate XXXII), with pink flush at tip which is sometimes as dark as Eugenia Red (Plate XIII).

*Peduncle.*—Strong; approximately 2 inches long.

*Calyx.*—Small; fairly simple; reflexes early; is usually pink-tinged inside, particularly near the petals.

Bloom:

*Borne.*—In truss-like or candelabra clusters containing from 3 to 7 flowers.

*Form.*—At first, full and high-centered much like the usual hybrid tea. Later it opens into shallow cup-shape with large center of stamens and pistils.

*Petalage.*—Double, with approximately 25 petals as an average.

*Color.*—Essentially white, but with a definite cream tinge particularly at the base of petals.

*Size.*—Large, measuring 4 to 4½ inches when fully open.

*Longevity.*—Lasts well on bush and as cut flower.

Petals:

*Texture.*—Silky.

*Size.*—Outer petals 1½ to 2 inches in each dimension.

*Fragrance.*—Mild tea fragrance.

*Persistence.*—Petals cling until flower dies.

Reproductive organs:

*Pistils.*—Many; tightly bunched in center of flowers; Martius Yellow (Plate IV).

*Stamens.*—Loosely bunched around pistils and rising to approximately the same height. Anthers—large; Mikado Orange to Orange Buff (Plate III). Filaments—graceful curved; Strontian Yellow (Plate XVI).

Having thus disclosed my invention, I claim:

The new and distinct variety of rose plant of the Grandiflora class, substantially as herein shown and described, characterized particularly by its vigor of growth; its exceptional productiveness of good blooms; its disease resistance; and its large, well-formed white blossoms borne in candelabra-like clusters.

No references cited.